United States Patent [19]

Smith et al.

[11] Patent Number: 4,874,499

[45] Date of Patent: Oct. 17, 1989

[54] ELECTROCHEMICAL MICROSENSORS AND METHOD OF MAKING SUCH SENSORS

[75] Inventors: Rosemary L. Smith; Scott D. Collins, both of Newton, Mass.

[73] Assignee: Massachusetts Institute of Technology, Cambridge, Mass.

[21] Appl. No.: 197,561

[22] Filed: May 23, 1988

[51] Int. Cl.$^4$ .............................................. G01N 27/30
[52] U.S. Cl. ........................................ 204/403; 156/60; 204/416; 204/418; 204/419; 204/420; 357/25
[58] Field of Search ............... 204/403, 416, 417, 418, 204/419, 420, 1 T; 357/25; 156/60

[56] References Cited

U.S. PATENT DOCUMENTS

| | | | |
|---|---|---|---|
| 3,915,829 | 10/1975 | Krebs ............................. | 204/420 X |
| 4,352,726 | 10/1982 | Sugano et al. ..................... | 357/25 X |
| 4,592,824 | 6/1986 | Smith et al. ....................... | 204/416 |
| 4,764,797 | 8/1988 | Shaw et al. ........................ | 357/25 |
| 4,773,970 | 9/1988 | Purbrick et al. .................... | 204/1 T |

OTHER PUBLICATIONS

J. F. Schenck, "A Field Effect Transistor Modified for use as a Sensor of Ions In Solution", Report No. 77CRD063, General Electric, May 1977.
Ho et al., "Encapsulation of Polymeric Membrane-Based Ion-Selective Field Effect Transistors,"-Sensors and Actuators, 4, 413, (1983).
Comte and Janata, "A Field Effect Transistor as a Solid State Reference Electrode," Anal. Chim. Acta., 101, 247 (1978).
Prohaska, "New Developments in Miniaturized Electrochemical Sensors" Technical Digest, International Conference on Solid-State Sensors and Actuators, Philadelphia Pa., Jun. 1985, pp. 401–402.
Blennemann et al., Transducers, '87, The Fourth International Conference on Solid–State Sensors and Actuators, pp. 723–725.
van den Vlekkert et al., Transducers, '87, The Fourth International Conference on Solid-State Sensors and Actuators, pp. 730–733.
Haemmerli et al., Anal. Chem., 52, 1179–1182, (1980).
Blackburn and Janata, J. Electrochem. Soc., 129(11), 2580–2584, (Nov. 1982).
Janata and Huber "Ion-Sensitive Field Effect Transistors" Ion-Selective Electrode Reviews, Applications, Theory and Development J. D. R. Thomas, ed., pp. 31–79, Pergamon Press, N.Y., (1979).
Buck and Hackleman, Anal. Chem., 49 (14), 2316–2321, (1977).

Primary Examiner—G. L. Kaplan
Attorney, Agent, or Firm—Kilpatrick & Cody

[57] ABSTRACT

Electrochemical microsensors formed of a substrate containing means for sensing potential or current, including active and passive electronic devices and electronic circuits, and a micromachined structure containing at least one cavity overlying the sensing means, wherein the structure and substrate are bonded together at a temperature less than about 400° C., in the absence of high voltage fields, using means not requiring highly planarized surfaces. A wide variety of materials can be utilized for both the substrate and overlying structure.

Diverse embodiments are possible, having in common a cavity containing a chemically sensitive material and means for sensing potential or current.

The resulting structural organization of materials transduces a chemical signal, such as concentration, to an electrical signal, which is then "processed" by the underlying FET or metallic connections. The present invention resolves the problems of the prior art in combining sensing devices with chemically sensitive material(s) to form a functional microsensor in a conveniently manufacturable fashion.

40 Claims, 4 Drawing Sheets

ELECTROCHEMICAL MICROSENSORS AND METHOD OF MAKING SUCH SENSORS

BACKGROUND OF THE INVENTION

This invention generally relates to electrochemical microsensors and methods for their assembly.

Specific, and often independently addressed, areas of electrochemical microsensor packaging and encapsulation are: electronic isolation from solution; lead attachment and encapsulation; and membrane attachment and isolation. Several solutions have been found for each individual problem area, but these often complicate the sensor fabrication process, making the process non-compatible with standard integrated circuit processing techniques. The resulting development and manufacturing costs are exorbitant, particularly for a multi-sensor device.

Chemical field effect transistors, or CHEMFETS, provide a means for sensing the concentration of chemical ions. The basis of operation of and FET is that a field is induced in the channel region which controls the conductivity between source and drain. Since the gate of a CHEMFET includes the surrounding solution, as well as any electrodes which bias the solution, isolation from the solution is as important to their proper functioning as is the isolation of MOS components and circuits from one another and from the environment. In addition, the surrounding solution is of changing chemistry, sensed by a change in gate potential. All interfaces with the solution have a characteristic potential which can alter interfacial processes, i.e., exchange currents, therein. Since FET fabrication is most readily accomplished using planar technologies, CHEMFET fabrication processes have traditionally employed solid state coatings with low water and ion permeability, such as silicon nitride and aluminum oxide, on the upper surface. Chemical vapor deposition (CVD) and patterning techniques for high-quality materials have been developed and perfected by the integrated circuit industry. However, processes must take into account that the substrate is exposed at the sides of the die after separation of the individual die from the silicon wafers. One way in which isolation of the exposed substrate can be accomplished is by encapsulation after die separation with an impermeable insulating material such as an epoxy resin or silicon nitride. More recently, diode isolation and SOI (silicon-on-insulator) techniques have been applied to the problems of substrate isolation.

Chemical microsensors, especially active devices such as the CHEMFET, require electrical signal and power supplying leads which communicate between the device in solution and the outer dry data acquisition environment. A means is therefore required by which leads can be attached to the chip and still be electrically isolated from one another and the ambient environment. Encapsulation of the leads from water and ions in the solution is required to prevent corrosion. Several approaches have been explored including commercially available bonding techniques such as wire bonding, tape automated bonding, etc. The physical bonding of the leads to the chip has not been as significant a problem as the difficulty in how to encapsulate the bonds and lead wires without covering the sensitive gate region. In one solution, the bonding pads for the CHEMFETs are placed along one edge of the chip, as far as possible from the active gate area.

Unfortunately, there are no suitable, commercially available chip carriers or cables for chemical microsensors. Printed circuit cards and dual lumen catheter are among the hand fashioned chip carriers and cabling that have been employed. While TAB bonding with commercially available Kapton TM tapes can reduce this problem, the adhesion layer fails the long-term exposure to ionic, aqueous solutions.

Other methods of lead attachment and encapsulation can be used. Photolithographically patterned material such as Riston TM can be used to protect the gate regions prior to wire bonding and encapsulation. Alternatively, back side contacts, which involve etching via holes through the wafer, diffusing dopants through the entire substrate by thermal gradient, or using SOI fabrication techniques, can be used. These methods place the lead attachment and encapsulation points on the back of the chip which need not be exposed to solution if an appropriate cell design can be employed. However, this has significant limitations: the complexity of processing the combination of back side contacts and on chip electronics (substrate) isolation; the limitations on the number and placement of i/o leads due to the large space required per contact and/or poor special resolution capabilities; the difficulties encountered in making IC fabrication compatible with back side contact formation; and the problem of in vivo sensors where both the chips and the leads are immersed in electrolyte.

Generally speaking, electrochemical microsensors either sense a potential, using selectively sensitive materials as transducers of chemical energy, or they measure the rate of a reaction, represented by the current. CHEMFETs are made chemically sensitive to a specific ion or other chemical species by attaching a sensing membrane material in series with a gate insulator.

It is crucial that the membrane integrity, adhesion and isolation from other sensing gates be maintained for each sensor. Since the chemically established membrane potential is effectively in series with any applied gate bias, it is sensed in the same manner as a change in the gate voltage of a FET. Any electrical shunt path, either vertical or horizontal, through or around the membrane/solution potential generating interface, will diminish the potential sensed by the FET or other active electronic device. Horizontal shunts between membrane covered FETs will create mutually dependent sensors and diminish their sensitivity.

A number of solutions to the problem of maintaining membrane integrity, adhesion and isolation have been proposed. The original approach was to use hand painted epoxy wells with silanization of surfaces to promote adhesion. It soon became apparent that this was not a commercially viable technique. A technique tried for membrane well fabrication which proved to not be commercially feasible is the Riston TM, E. I. Dupont de Nemours & Co., Wilmington, DE, masking technique, described by Ho, et al., in "Encapsulation of polymeric membrane-based ion-selective field effect transistors", *Sensors and Actuators* 4,413 (1983). Attempts to improve adhesion of subsequently solvent cast polymeric membrane materials included using microfabricated meshes made in spun cast polyimide films or membranes formed by spin casting of a plasticized polymeric matrix onto a wafer containing FETs or thin film electrodes, followed by local doping of the organic film with an ion sensitive material such as an ionophore.

Unfortunately, all of these techniques preclude the use of liquid membrane materials and the fabrication in miniature of a classical ion sensing electrode (ISE) (i.e. membrane/filling solution/redox couple/metal/amplifier). ISE-like devices are desirable since each interface in the electrochemical system is thermodynamically well defined and could therefore be fabricated in such a way as to minimize drift and enhance reproducibility. Conventional CHEMFETs have a semiconductor/ insulator/ ionic solution or semiconductor/ insulator/ membrane/ ionic solution gate structure. The coupling between ionic and electronic conduction in these systems is unclear. The insulator/membrane interface is blocked, impermeable to membrane charge transfer, and therefore not thermodynamically well defined. Modifications of CHEMFET structures to include an inner reference solution and redox couple between the membrane and gate insulator could result in a highly improved chemical microsensor.

CHEMFETs were first modified to include and inner reference solution and redox couple between the membrane and gate insulator in 1978, as described by Comte and Janata, "A Field Effect Transistor as a Solid State Reference Electrode", Anal. Chim. Acta. 101, 247 (1978). They laboriously pasted individual capillary tips over the gate region of CHEMFETs, epoxied them in place and then filled them with a pH buffer solution, entirely by hand, to create a reference FET.

In 1985, Prohaska described surface micromachining silicon nitride microchambers to form thin film, nearly planar, electrochemical cells ("New Developments in Miniaturized Electrochemical Sensors", Technical Digest, International Conference on Solid-State Sensors and Actuators, Philadelphia, PA, June 1985, pp. 401–402).

Micromachining of chambers in Pyrex TM glass plates using etching and laser drilling was described in two more recent papers by Blennemann, et al., Transducers '87, The Fourth International Conference on Solid-State Sensors and Actuators, pp. 723–725 and "Glass Encapsulation of Chemical Solid-State Sensors Based on Anodic Bonding", van den Vlekkert, et al., Transducers '87, pp. 730–733 (1987). The micromachined structures were anodically bonded to the FET containing substrate at temperature typically of around 400° to 600° C. with voltages of around 600 to 1,000 volts.

The process using anodic bonding of machined Pyrex TM structures has a number of drawbacks, principally related to the use of the anodic bonding. Care must be taken to avoid damaging the electronic and sensor components during bonding due to large, electrostatic fields and heat. Another problem is the requirement for a planar substrate surface, of less than 1000 angstroms steps, to insure uniform bonding between the Pyrex TM structure and the silicon substrate. Conventional pattern transfer techniques do not produce a surface sufficiently smooth to insure proper bonding. Further, the material which is bonded to the substrate is limited to a material having essentially the same coefficient of expansion as the substrate so that the materials do not separate upon cooling following the bonding process. Some of these problems are discussed by both Blennemann at p. 723 and by van den Velkkert at p. 730.

It is therefore an object of the present invention to provide electrochemical microsensors which can use liquid membrane materials which can be fabricated with structures functionally equivalent to classical ion sensing electrodes.

It is further object of the present invention to provide methods for assembly and packaging of electrochemical microsensors which do not require high temperatures.

It is another object of the present invention to provide electrochemical microsensors whose chemical transducing structures and their containment can be fabricated independently from any passive or active electronic devices.

It is a further object of the present invention to provide electrochemical microsensors having a variety of three-dimensional forms and variability of function.

It is still further object of the present invention to provide electrochemical microsensors having a geometric configuration which avoids problems with wire bond encapsulation.

It is another object of the present invention to provide electrochemical microsensors containing liquid electrolyte, selective and responsive biological or labile materials, and methods for their manufacture.

SUMMARY OF THE INVENTION

Electrochemical microsensors formed of a substrate containing means for sensing potential or current, such as an active or passive electronic device or a circuit, and a micromachined structure containing at least one cavity overlying the conducting means, wherein the substrate and micromachined structure are bonded together using organic adhesives, thermoplastics, low temperature CVD or spin-on glasses. Neither the organic adhesives, LT oxides not the thermoplastics require high temperatures, in excess of 400° C., high voltage fields or highly planarized surfaces. Further advantages over the prior art devices are that active electronic devices including FETS can be placed at the sensing site to improve the signal to noise ratio and that a wider variety of materials can be utilized for both the substrate and overlying structure.

Diverse embodiments are possible, having in common a cavity open to the environment containing a chemically sensitive material and means for sensing potential or current.

The construction and operation of one embodiment, a CHEMPOT containing liquid ion exchanger for the measurement of serum calcium, is described. The packaging of the sensor began with a four-inch silicon wafer containing approximately 2500, 1.46×1.87 mm die. Every third die contained a single n MOS CHEMFET in a p-well. The wafers were processed commercially following a metal gate CMOS process and included a top surface layer of LPCVD silicon nitride before metalization. The CHEMPOT and bonding area patterns were photolithographically transferred onto both sides of an oxided <100> two-inch diameter, double-sided polished silicon wafer. Oxide was removed from the patterned silicon and the exposed silicon anisotrophically etched. The underside of the wafer, which would be attached to the sensor wafer, was coated with epoxy and the machined wafer and sensor wafer aligned and adhered. The sandwiched structure was diced after curing the epoxy and individual die glued to a printed circuit card. Aluminum wires were wedge-bonded to the bonding pads on the chip and to the copper leads of the PC card. The wires were coated in epoxy and the CHEMPOT loaded with liquid ion exchanger for serum calcium ion. Testing shows that the CHEMPOTS exhibit similar sensitivity and reproducible response to an Orion macroelectrode containing the same liquid ion exchanger.

Other embodiments which are described include a multi-sensor device and a device consisting of two cavity-containing structures, one for liquid electrolyte and one for ion-selective polymer.

BRIEF DESCRIPTION OF THE DRAWINGS

FIG. 3 is a schematic cross-sectional view of a micromachined ion sensor and reference electrode multi-device chip, according to the present invention.

DETAILED DESCRIPTION OF THE INVENTION

The most important advantage of the present invention is the flexibility of construction. Utilization of adhesive to connect a micromachined cavity containing structure to the underlying substrate containing means for sensing potential or current allows the device to be constructed at a low temperature. It also eliminates the requirement that the materials for making the machined structure and underlying substrate with electronic devices of materials have essentially the same coefficient of expansion. Other advantages revolve around the ability to include a liquid electrolyte which permits fabrication of structures functionally equivalent to classical ISE. Incorporation of biologically active and labile materials, including lipid membranes and proteins is also possible. Further, complex devices can be constructed, including multi-chambered devices.

The microchemical sensors of the present invention have a variety of uses. For example, they may be used for in vivo measurements of hydrogen, sodium, potassium, calcium, carbonate and other ion levels, as well as for measuring protein concentration. Other applications include gas monitoring, for example, in the cockpits of airplanes or other situations where monitoring is important, in food processing, in separations technology and in one-line monitoring during industrial processing.

Due to the batch processing method of manufacture, the devices are economical enough to be disposable. A significant advantage over the devices constructed by anodic bonding of machined Pyrex TM structures to substrate containing electronic devices are that the high field and temperatures required for bonding which are very detrimental to thin film electrode materials such as silver and to MOSFET devices without gate protection are avoided. There is also no requirement for an extremely planar surface on the electronic device containing substrate. This is significant economically since standard processing techniques will not yield a surface of sufficient planarity for good anodic bonding.

Another important aspect of the design is that it is standard enough to utilize foundry services. The substrate containing the sensing means can be formed using conventional integrated circuit processing techniques. Essentially any means for sensing and transmitting potential or current from the sensing site can be utilized. Examples include passive electronic devices such as thin film conductors and resistors, active electronic device such as transistors including FETS and diodes, and electric circuits. In general, these devices will be in the form of a CHEMFET, consisting of a source and drain separated by a gate region whose conductivity is altered by changing electrical potential across the gate insulator, although any other conductor may also be sufficient, depending on the application. Electronic isolation is achieved by diode isolation. Either the sensing FETs and all other on-chip circuitry are of a single type, i.e., nMOS or pMOS, and placed in the opposite well, or a twin tub CMOS or silicon on insulator technology is employed. The FETs can have polysilicon gates, as long as the gates are or can be electrically floated. The top surface of the sensor chip is completely coated with silicon nitride, or other encapsulating, material except for the bonding pads. All conducting lines are beneath this layer.

In the preferred embodiment, the cavity containing structure is formed by micromachining, using either a laser or drill, ion milling or by chemical etching. The term "micromachined", as used herein with respect to a cavity containing structure, is to be construed to mean a structure configured using any process which can produce small three dimensional structures with a high degree of positional and geometric accuracy. Materials which can be utilized to form the structure include Pyrex TM, Fotoform glass (obtained from Corning, N.Y.), silicon and organics such as the photostructurable Novolac TM resins manufactured by Rohm and Haas, Spring House, PA.

The Fotoform material is photopatternable via exposure to UV light and subsequent chemical etching. Holes with diameters as small as 0.001 inch can be achieved using this material. The processed glass is transparent, making alignment easy and allowing the use of a photocurable epoxy or silicon as the adhesive layer. Silicon has several advantages over the Fotoform glass. Fine geometrical control in all three dimensions is possible using anisotrophic etchants. Etch stopping techniques for anisotrophic and isotrophic etchants are known to those skilled in the art. Flow channels and valves can also be incorporated into the machined substrates to aid in filling and for flow analysis. Silicon is a superior mechanical material over glass, and therefore is preferred if movable parts are utilized.

A variety of adhesives can be used to bond the cavity containing structure to the active electronic device containing substrate. Materials include epoxy, polyimide, silicon rubber, and spin-on glass (Accuglass TM, Allied Chemical Corp., N.Y.). The latter is a suspension of alkoxysilanes in an organic solution which is spun like a photoresist onto the substrate and hydrolyzed to form a coherent glass film, the cavity containing structure is aligned as desired, and the material cured and solvent removed at a temperature of approximately 200° to 250° C. In general, the preferred materials are those which can be used to bind the two surfaces at a temperature of less than about 400° C. A temperature of less than 200° to 300° C. is preferred so that materials having different coefficients of expansion can be utilized. There is also a greater problem with diffusion of aluminum into the silicon substrate at temperatures higher than 300° C.

Materials which are useful for encapsulating the completed sensor to protect it from the external environment include silicon nitride, aluminum oxide, tantalum oxide, silicon dioxide, polyimide, silicones, and epoxy resins.

A variety of ion or molecule sensitive materials can be utilized within the cavity of the device to determine the specificity of the sensor. For example, liquid polyether ester tetraphenyl borate and sodium silicates are selective for $Na^+$. A commercially available material selective for $K^+$ is valinomycin.

Several solid state membrane materials exist, such as $LaF_3$, $AgCl$ and $Si_3N_4$, which establish potentials selectively to fluoride, chloride and hydrogen ions, respectively. Many of the solid state materials, such as silicon nitride and aluminum oxide, which are used as hydrogen ion sensitive membranes are also insulators and excellent diffusion barriers to water and ions. They are often incorporated as the upper most layer of the FET gate insulator and as an encapsulant. They can also be integrated into the FET fabrication at the wafer level.

Organic membranes are employed for sensing most other organic chemical species. There are a host of different organic membrane systems which are selective to a wide variety of ions which can be attached to the FET gate insulator by physi-chemical adhesion.

Other membrane structures, including lipid bilayers and novel biologically based matrices, can also be employed. These membranes can be doped with antibiotics, proteins, or other materials which selectively interact or react with the molecule to be sensed. Diverse variations of this type of sensor, which employ secondary transduction mechanisms, are also possible. One such example consists of incorporating enzymes or catalysts into the membrane structure. Sensing of the enzyme substrate may be indirectly accomplished by monitoring the rate of formation of products or depletion of reactants during the enzymatic or catalytic reaction. This scheme is commonly used in the electrochemical detection of glucose. Here, glucose oxidase (GOD) is immobilized into a membrane via covalent or physical attachment. The catalysis of glucose to gluconic acid by glucose oxidase produces hydrogen peroxide and $H^+$. Under substrate limiting conditions, detection of hydrogen peroxide or pH is directly related to the detection of glucose. Multiple enzyme systems can also be employed.

Example 1: Construction and application of a Calcium Selective Microsensor.

Fabrication:

The packaging of the sensor began with a 4-inch wafer containing approximately 2500, 1.46×1.87 mm die. Every third die contains a single n MOS CHEMFET in a p-well. The wafers were processed commercially (Solid State Scientific) following a metal gate CMOS process, with final process step additions to include a 0.2 $\mu$ thick, top surface layer of LPCVD silicon nitride prior to bonding pad metal layer deposition. The mask layout for the micromachined package was designed, and dimensions were assigned in accordance with the FET containing wafer layout.

Micromachined cavities for membranes were positioned over the CHEMFET gate and large openings were positioned over the bonding pad area. The latter were positioned such that the borders of the opening were just at the edge of the scribe lanes. With this configuration, after the attachment of the micromachined substrate, individual sensor die-plus-membrane-holders could be separated with a diamond diesaw. The term "CHEMPOT" is used to designate structures consisting of the die-plus-membrane holders, in contrast to the devices containing the ion selective material.

The CHEMPOT and bonding area patterns were photolithographically transferred onto both sides of an oxidized, <100> two-inch diameter, double-side polished silicon wafer with the aid of an infrared aligner. The oxide was removed from the patterned areas in hydrofluoric acid. The wafer was then placed in KOH at 60° C. where exposed silicon was anisotrophically removed from both sides of the wafer. Etching was terminated when the pyramidal pits forming on either side met one another approximately midway through the wafer.

The underside of the micromachined wafer, subsequently attached to the sensor wafer, was then coated with epoxy. This was accomplished by applying a thin film of epoxy onto a glass slide, placing the underside of the machined wafer onto the epoxy coated slide, and then gently pulling the wafer and slide apart. More controllable techniques such as screen printing, spray coating or photopatterning, and other materials could be employed. The machined 2-inch wafer and ¼ of the 4-inch sensor wafer were then aligned with respect to one another under a microscope with an x-y-z positioning stage and a vacuum pickup arm. A manual, contact type wafer aligner can readily be used for this procedure, with the machined wafer replacing what is normally the mask.

When aligned, the two wafers were brought into contact and left at room temperature to partially cure for 12 hours, and then completely cured at 80° C. The sandwiched structure was then diced, the individual die glued to a printed circuit card and aluminum wires wedge-bonded to the bonding pads on the chip and to the copper leads of the PC card. The wires were then coated in epoxy, which was dispensed from a needle. This second application of epoxy was then fully cured.

Figure 1:
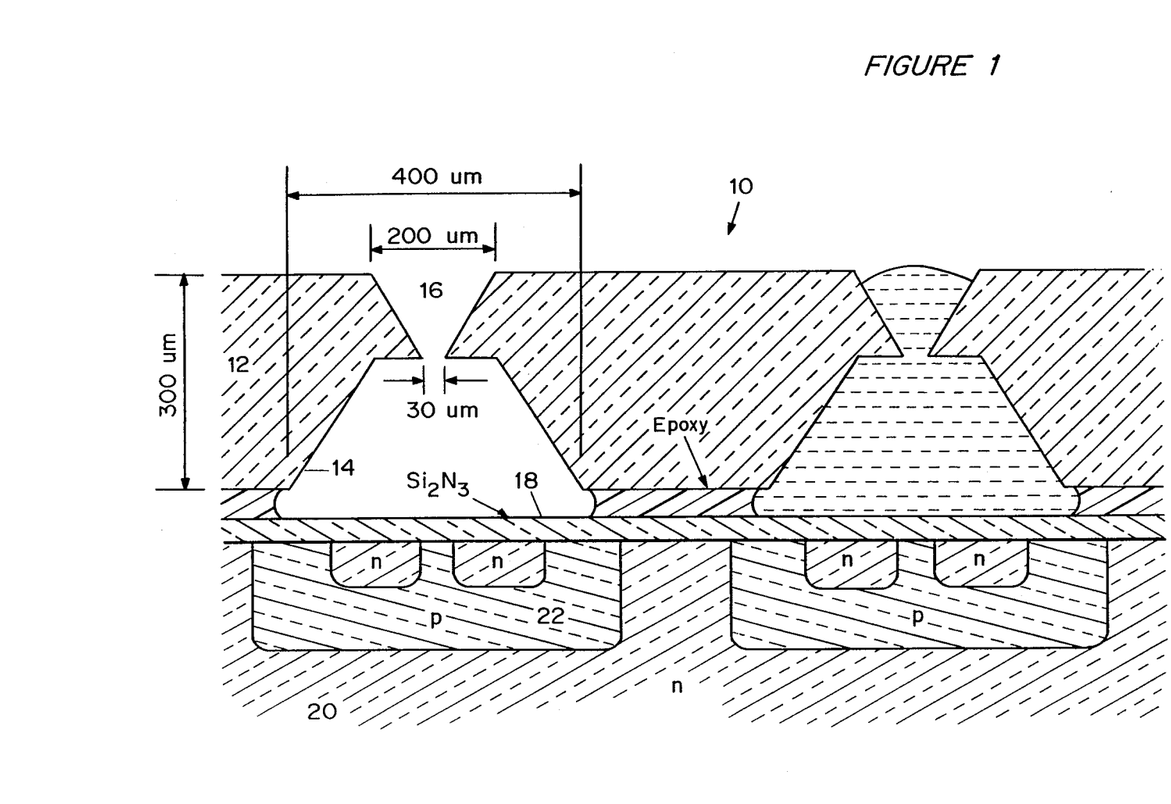
FIG. 1 is a cross-section view of the micromachined package according to the present invention, described in example 1, indicating the positioning of membrane chambers with respect to the underlying CHEMFET gates and approximate dimensions.

As shown schematically in FIG. 1, the finished device 10 consists of a machined silicon structure 12 (approximately 300 $\mu$ thick), containing a cavity 14 (400 $\mu$ diameter) exposed to the substance to be sensed through a funnel-shaped opening 16 (30 $\mu$ expanding upward to 200 $\mu$ in diameter), adhered by an epoxy layer 18 to a substrate 20 containing a n MOS CHEMFET in a p-well 22. The structure 12 provided an excellent barrier to the flow of epoxy into the gate region during encapsulation of wire bonds. Electrochemical Testing:

The CHEMPOTs were loaded with a liquid ion exchanger for serum calcium ion (Orion membrane number 9825) by positioning the liquid over the chamber opening while applying vacuum to evacuate the air inside the chamber. Upon release of the vacuum, the liquid fills the chamber. An Orion barrel electrode was charged with the same membrane material and tested along with the CHEMPOT for comparison. Both sensors were titrated with $CaCl_2$ in a constant background electrolyte of 0.2 M KCl. All potentials are referenced to a Saturated Calomel Electrode (SCE). The CHEMFET was operated in a feedback mode. All measurements were made at room temperature 24° C.

Figure 2:
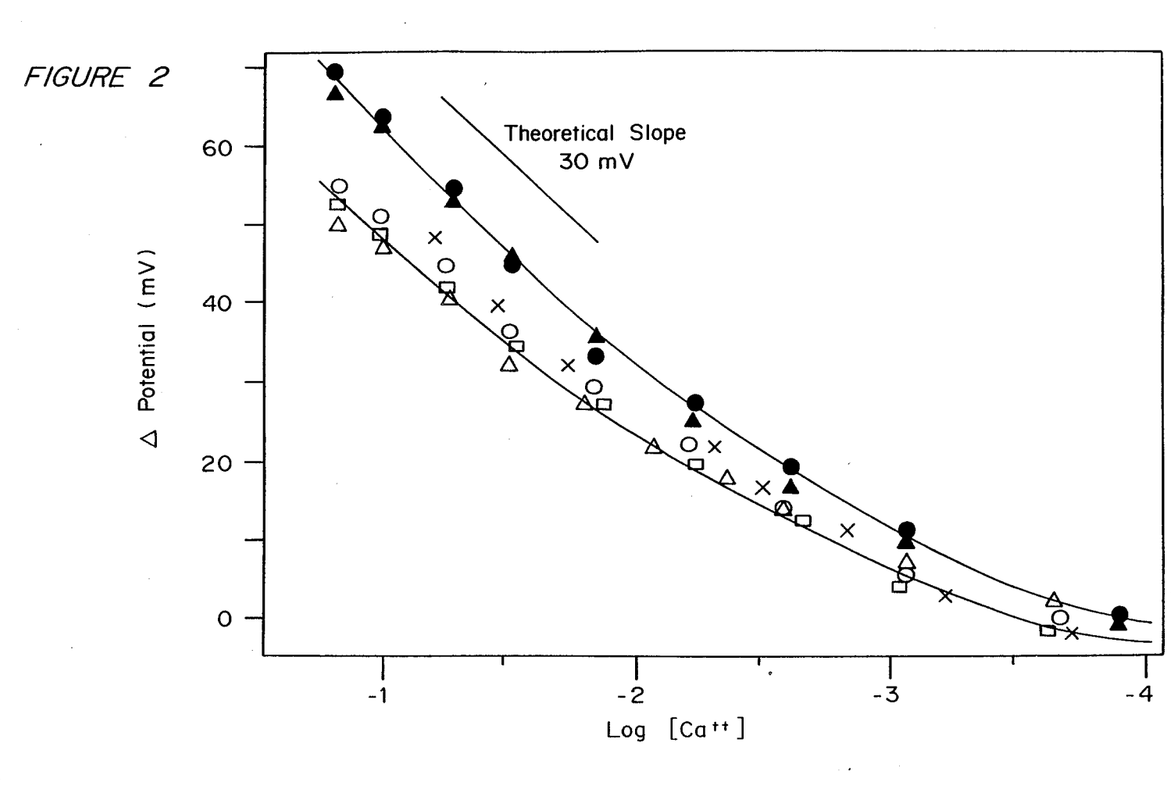
FIG. 2 is a graph of the change in potential (mV) versus log of $[Ca^{++}]$ for several titrations as measured by an Orion electrode ( ) and by electrochemical microsensors $(+, o, \Delta \square)$ according to the present invention.

Results:

The response of the CHEMPOT and the Orion macro electrode to calcium ion concentration is shown in FIG. 2. The Orion electrode gives a linear response to $Ca_{++}$ in the range from 0.01 to 0.1 M, with a slope equal to the theoretical value of 30 mV/pH. Although the CHEMPOT shows a slightly lower sensitivity (27 mV/pH) than the Orion macro electrode, its response is very reproducible. The CHEMPOT gave an identical response to a repeated titration after 24 hours immersion in a solution containing 0.1 M $CaCl_2$ and 0.2 M KCl.

The CHEMPOT drift reached a steady state value of less than 0.1 mV/hr after the first hour of exposure to solution. This level of drift was maintained for the next 5 days, during which time it continued to respond to additions of $CaCl_2$.

It was noted that the CHEMPOT was sensitive to rigorous movement, such as shaking, but the gate potential always returned to its original value (with 1 mV), even after repeated removal from solution and biasing. This is highly unusual for unshielded FET sensors, and may mean that the silicon package provides some electrostatic shielding. The conductivity of the package may also explain the slightly lower sensitivity of the CHEMPOT, i.e., an electrical shunt path across the membrane through the conductive silicon package may exist. This is indeed possible since the package demonstrated here has no insulating layer, other than native oxide, on the inner walls of the membrane chamber. This can be remedied by oxidation and/or the application of LPCVD silicon nitride after micromachining the package.

Example 2: Design and Fabrication of a Sensor Package incorporating fill channels.

The incorporation of fill channels allows for the construction of a microminiature ISE configuration over an FET. The chemically sensitive structure is shown in FIG. 3 along with a reference FET which incorporates a porous membrane. The assembly of this package is the same as for the CHEMPOTs, with the following differences: the PVC (or other polymer matrix) membranes are cast into the chambers and cured before attachment to the FET containing wafer and then, after wafer bonding, dicing, lead attachment and encapsulation, the chambers are individually filled with electrolyte.

Figure 3A:
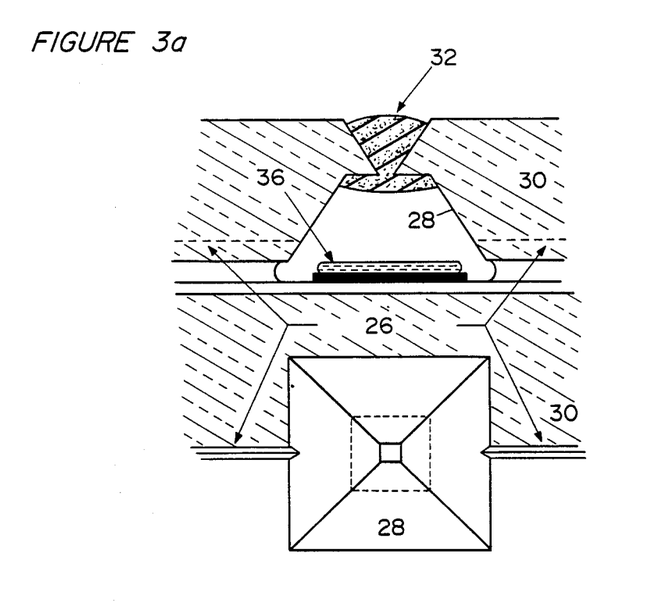
FIG. 3A is a bottom view of the device demonstrating the location of fill channels.
Figure 3B:
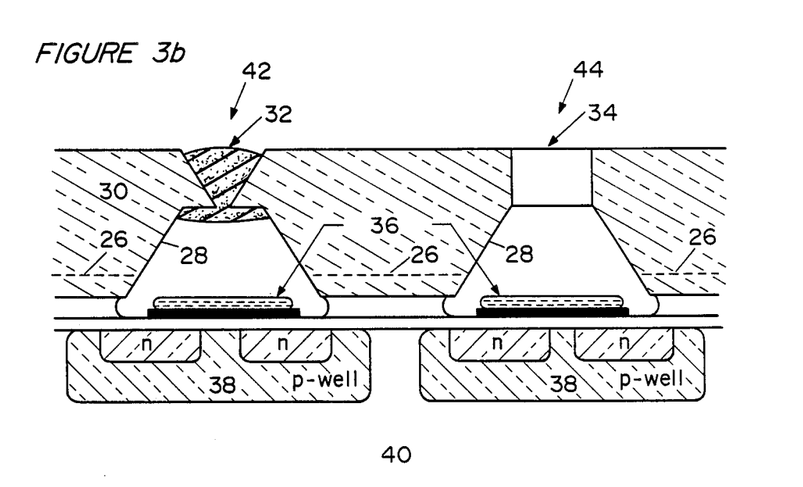
FIG. 3B is a side view of the juxtaposed devices.

As shown in FIG 3A, fill channels 26 extending into the cavity 28 are micromachined in the structure 30. Chemically sensitive polymeric membrane 32 is cast in the opening to the cavity 28. An Ag/AgCl electrode 36 is provided over the FETS 38 in the underlying silicon substrate 40. A porous membrane 34 provides an opening to the cavity 28 of device 44. The structure 30 is adhered to the substrate 40 and the cavities 28 filled with KCl electrolyte solution.

As constructed, device 42 with the ion selective polymeric membrane 32 acts as an ion sensor and device 44 with the porous membrane 34 acts as a reference field effect transistor (REFET). Device 42 with membrane 32 has a structure functionally identical to a classical ISE. Device 44 with porous membrane 34 has a structure functionally identical to a classical liquid junction reference electrode.

Example 3: Design and Fabrication of a Sensor Package having two or more Separately Machined Structures.

Figure 4:
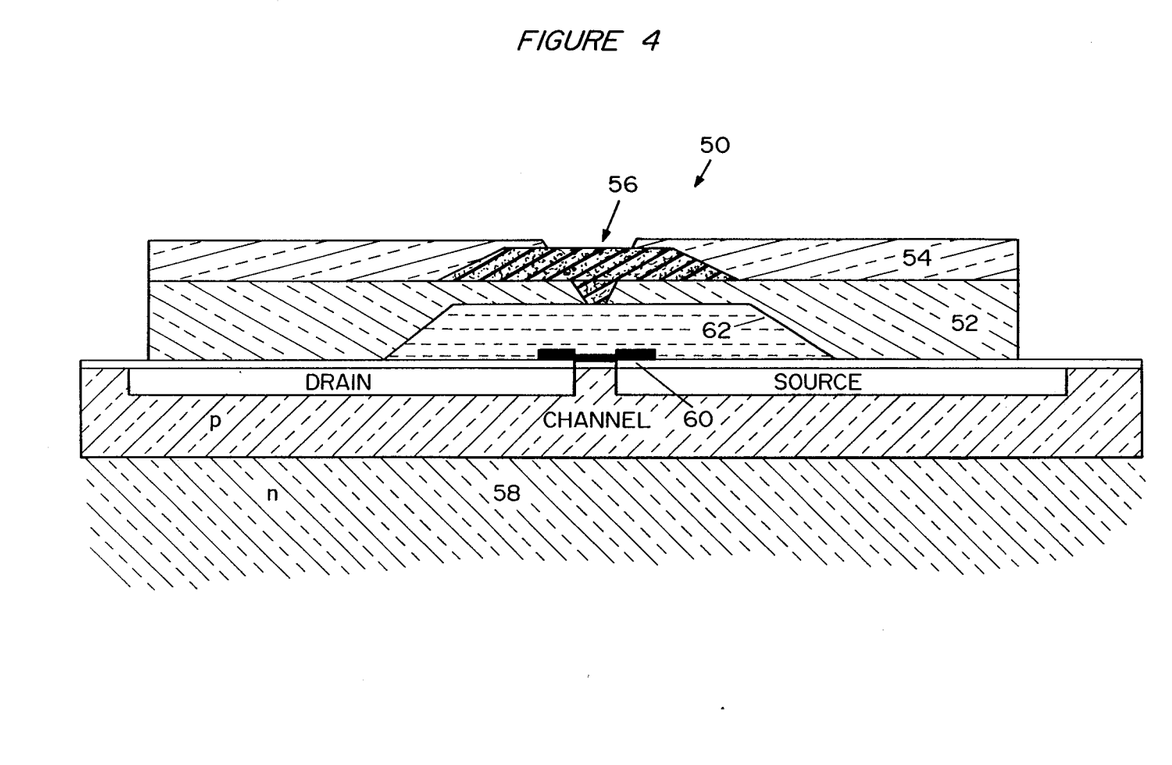
FIG. 4 is a cross-sectional view of a micromachined package having separately machined structures with a cavity containing polymeric membrane and a cavity containing an electrolyte, according to the present invention.

As depicted in FIG. 4, a device 50 with two separately machined cavity containing structures 52, 54 can be constructed using the method of the present invention. This device represents a significant advancement over the devices possible with prior art methods. Polymeric membrane 56 is cast into one machined structure 54 which is then adhered to the top of a second machined structure 52. The second structure 52 can be adhered to the device containing substrate 58 before or after the structure 54 is adhered. In the preferred embodiment, an Ag/AgCl electrode 60 is placed under the cavity 62 in the structure 52 adjacent to the substrate 58. The cavity 62 is then filled with electrolyte.

More complex and varied devices can be constructed using the methods described above. Multi-sensor devices in conjunction with reference electrodes can also be constructed, also using the methods described above.

Modifications and variations of the present invention, methods for manufacturing chemical microsensors, and the products thereof, will be obvious to those skilled in the art from the foregoing detailed description of the invention. Such modifications and variations are intended to come within the scope of the appended claims.

We claim:

1. An electrochemical microsensor comprising:
   a substrate containing microelectronic means for sensing potential or current;
   a micromachined structure having openings extending into a cavity therein from opposite sides of the structure, wherein said structure has been produced by photolithographic transfer of a two dimensional pattern onto a material to form a three dimensional structure following selective removal of the material; and
   wherein the structure containing the cavity has been positioned over the substrate so that an opening into the cavity extends over the sensing means and the cavity containing structure has been adhered to the substrate using a process which simultaneously adheres multiple structures to substrates as a single unit, with an adhesive forming a seal between the substrate and structure at a temperature less than approximately 400° C.

2. The device of claim 1 wherein the material for the machined structure is selected from the group consisting of silicon, glass, and micromachinable organic materials.

3. The device of claim 1 further comprising a material having a specific chemical reactivity in the cavity of the structure.

4. The device of claim 3 wherein the material is selected from the group consisting of solid state materials, biological materials, and combinations thereof.

5. The device of claim 4 wherein the material is selected from the group consisting of valinomycin, liquid polyether ester tetraphenyl borate, silver chloride, $LaF_3$, $Si_3N_4$, pH sensitive glass, aluminum oxide, lipid bilayers, lipid bilayers doped with antibiotics, and combinations of proteins and lipid bilayers.

6. The device of claim 3 wherein the chemically sensitive material is cast into the cavity of the machined structure to form a second cavity between the material and the substrate.

7. The device of claim 1 wherein the sensing means is a electronically active device.

8. The device of claim 7 wherein the sensing means is a transistor.

9. The device of claim 1 wherein the sensing means is a passive electronic device.

10. The device of claim 9 wherein the sensing means is a conductive film.

11. The device of claim 1 wherein the sensing means is a circuit.

12. The device of claim 1 further comprising a reference electrode.

13. The device of claim 1 further comprising an electrolyte.

14. The device of claim 1 wherein the cavity containing structure is adhered to the substrate with an adhesive selected from the group of organic adhesives, and spin on glass.

15. The device of claim 14 wherein the adhesive is selected from the group consisting of a photocurable epoxy or silicon.

16. The device of claim 1 further comprising means for connecting the microsensor to an external electrical circuit.

17. The device of claim 1 for sensing a molecule in a solution wherein the sensor is encapsulated with a coating impermeable to the solution.

18. The device of claim 17 wherein the coating is selected from the group consisting of silicon nitride, aluminum oxide, tantalum oxide, silicon dioxide, polyimide, silicones, and epoxy resins.

19. The device of claim 1 further comprising at least one cavity containing structure adhered to the upper surface of the cavity containing structures overlying the substrate.

20. The device of claim 19 further comprising electrolyte wherein the chemically sensitive material and electrolyte are in separate cavities.

21. A multi-sensor device comprising electrochemical microsensors having
   a substrate containing microelectronic means for sensing potential or current;
   a micromachined structure having opening extending into a cavity therein from opposite sides of the structure, wherein said structure has been produces by photolithographic transfer of a two dimensional pattern onto a material to form a three dimensional structure following selective removal of the material, and;
   wherein the cavity containing-structure has been positioned over the substrate so that an opening into the cavity extends over the sensing means and the cavity containing structure has been adhered to the substrate using a process which simultaneously adheres multiple structures to substrates as a single unit, with an adhesive forming a seal between the substrate and structure at a temperature less than approximately 400° C.; and
   a chemically sensitive material within the cavity;
   wherein the electrochemical microsensors contain materials having chemical sensitivities to different chemical species.

22. The device of claim 1 encapsulated for measuring the concentration of chemical species in a solution or gas.

23. A method for manufacturing a chemical microsensor comprising:
   (i) providing a substrate containing microelectronic means for sensing potential or current;
   (ii) providing a micromachined structure having openings extending into a cavity therein from opposite sides of the structure, wherein said structure has been produced by photolithographic transfer of a two dimensional pattern onto a material to form a three dimensional structure following selective removal of the material, and;
   (iii) positioning the structure containing the cavity over the substrate wherein an opening into the cavity extends over the sensing means; and
   (iv) using a process to adhere the cavity containing structure to the substrate which simultaneously adheres multiple structures to substrates as a single unit, at a temperature less than approximately 400° C.

24. The method of claim 23 further comprising selecting the material for the machined structure from the group consisting of silicon, glass, and photoreactive organics.

25. The method of claim 23 further comprising providing a material having a specific chemical reactivity in the cavity of the structure.

26. The method of claim 25 further comprising selecting the material from the group consisting of valinomycin, liquid polyether ester tetraphenyl borate, silver chloride, $LaF_3$, $Si_3N_4$, pH sensitive glass, aluminum oxide, lipid bilayers, lipid bilayers doped with antibiotics, and combinations of proteins and lipid bilayers.

27. The method of claim 25 wherein the material is cast into the cavity of the machined structure to form a second cavity between the material and the substrate.

28. The method of claim 23 wherein the sensing means is an electronically active device.

29. The method of claim 28 wherein the sensing means is a transistor.

30. The method of claim 23 wherein the sensing means is a passive electronic device.

31. The method of claim 30 wherein the sensing means is a conductive film.

32. The method of claim 23 wherein the sensing means is a circuit.

33. The method of claim 23 further comprising providing a reference electrode.

34. The method of claim 23 further comprising providing an electrolyte.

35. The method of claim 23 wherein the cavity containing structure is adhered to the substrate with an adhesive selected from the group of organic adhesives, and spin on glass.

36. The method of claim 23 further comprising encapsulating the sensor with a coating impermeable to the external environment.

37. The method of claim 36 wherein the coating is selected from the group consisting of silicon nitride, aluminum oxide, tantalum oxide, silicon dioxide, polyimide, silicones, and epoxy resins.

38. The method of claim 23 further comprising adhering additional cavity containing structures to the cavity containing structures overlying the device containing substrate.

39. The method of claim 38 further comprising providing material sensitive to different chemical species and electrolyte in separate cavities.

40. The method of claim 39 further comprising placing the devices on a single chip.

* * * * *

UNITED STATES PATENT AND TRADEMARK OFFICE
CERTIFICATE OF CORRECTION

PATENT NO. : 4,874,499
DATED : October 17, 1989
INVENTOR(S) : Rosemary L. Smith; Scott D. Collins It is certified that error appears in the above-identified patent and that said Letters Patent is hereby corrected as shown below:

```
Column 1, line 22:  After "operation of" replace "and" with
                    -- any --.
Column 2, line 7:   After "fails" replace "the" with -- with --.
Column 3, line 18:  Replace "and" with -- an --.
Column 3, line 43:  Replace "temperature" with
                    -- temperatures --.
Column 4, line 12:  Insert --a-- before "still further".
Column 4, line 30:  Replace "not" with --nor--.
Column 5, line 6:   Replace "cross-section" with
                    -- cross-sectional --.
Column 5, line 14:  Replace "()" with -- (●, ▲) --.
Column 5, line 55:  Replace "one-line" with -- on-line --.
Column 5, line 60:  Replace "substrate" with -- substrates --.
Column 6, line 9:   Replace "device" with --devices --.
Column 8, line 54:  Move "Electrochemical Testing:" to
next line as a Heading.
Column 10, line 64: Replace "a" with --an--.
Column 11, line 28: Replace "surface" with -- surfaces --.
Column 11, line 37: Replace "opening" with -- openings --.
Column 11, line 39: Replace "produces" with -- produced--.
```

Signed and Sealed this

Tenth Day of May, 1994

BRUCE LEHMAN

Attest:

Attesting Officer

Commissioner of Patents and Trademarks